United States Patent [19]
Bristow et al.

[11] Patent Number: 5,817,866
[45] Date of Patent: Oct. 6, 1998

[54] PROCESS FOR THE ACETOXYLATION OF OLEFINS

[75] Inventors: Timothy C. Bristow, Beverley; Simon J. Kitchen, Hatfield; David Newton, Guildford, all of United Kingdom

[73] Assignee: BP Chemicals Limited, London, England

[21] Appl. No.: 988,448

[22] Filed: Dec. 10, 1997

[30] Foreign Application Priority Data

Dec. 10, 1996 [GB] United Kingdom .................. 9625599

[51] Int. Cl.$^6$ .................................................. C07C 67/05

[52] U.S. Cl. ............................................................ 560/245

[58] Field of Search ............................................. 560/245

[56] References Cited

U.S. PATENT DOCUMENTS

| | | | |
|---|---|---|---|
| 3,670,014 | 6/1972 | Fernholz | 560/245 |
| 5,550,281 | 8/1996 | Cirjak | 560/245 |
| 5,710,318 | 1/1998 | Cirjak | 560/245 |

FOREIGN PATENT DOCUMENTS 0 685 449 A1  12/1995  European Pat. Off. .

*Primary Examiner*—Michael L. Shippen
*Attorney, Agent, or Firm*—Nixon & Vanderhye

[57] ABSTRACT

A process for the production of vinyl acetate which comprises reacting at elevated temperature in a fluid bed reactor ethylene, acetic acid and an oxygen-containing gas in the presence of a fluid bed catalyst material wherein a liquid is introduced into the fluidised bed reactor for the purpose of removing heat therefrom by evaporation of the liquid.

13 Claims, No Drawings

PROCESS FOR THE ACETOXYLATION OF OLEFINS

The present invention relates in general to a fluid bed process for the acetoxylation of olefins or diolefins and in particular to a fluid bed process for the production of vinyl acetate from ethylene, acetic acid and an oxygen—containing gas in the presence of a fluid bed catalyst.

Fluid bed processes for the production of vinyl acetate from ethylene, acetic acid and an oxygen—containing gas in the presence of a fluid bed catalyst are known from, for example, EP-A-0685449, EP-A-0685451 and EP-A-0672453.

EP-A-0685449 discloses a process for manufacturing vinyl acetate in a fluid bed reactor comprising feeding ethylene and acetic acid into the fluid bed reactor through one or more inlets, feeding an oxygen—containing gas into the fluid bed reactor through at least one further inlet, co-joining the oxygen—containing gas, ethylene and acetic acid in the fluid bed reactor while in contact with a fluid bed catalyst material to enable the ethylene, acetic acid and oxygen to react to produce vinyl acetate and recovering the vinyl acetate from the fluid bed reactor.

EP-A-0685451 discloses a method for the preparation of fluidisable catalyst having the formula Pd—M—A where M comprises Au, Ba, Cd, Bi, Cu, Mn, Fe, Co, Ce, U or mixtures thereof, A comprises an alkali metal or mixture thereof and M is present in the range of from 0 to about 5 wt. % and A is present in the range of greater than 0 to about 10% by weight which is useful in the acetoxylation of olefins and diolefins in a fluid bed reactor comprising:

(a) preparing a fixed bed catalyst precursor consisting primarily of Pd—M supported on a fixed bed catalyst support, (b) milling the fixed bed catalyst precursor with a fluid bed catalyst binder to form a slurry, (c) drying the slurry to form microspheroidal particles of solid fluid bed catalyst precursor, and optionally, (d) impregnating the microspheroidal particles of fluid bed catalyst precursor with a solution of an alkali metal salt to produce a fluid bed catalyst.

EP-A-0672453 discloses a support for the manufacture of a vinyl acetate catalyst comprising a mixture of substantially inert microspheroidal particles having a pore volume of between 0.2 to 0.7 cc/g, a surface area of between 100 to 200 $m^2/g$ and at least 50% of said particles are less than 100 microns.

The manufacture of vinyl acetate from ethylene, acetic acid and oxygen is an exothermic reaction and it is therefore necessary to provide means to cool the fluidised bed reactor to remove the heat liberated. Failure to do so would eventually lead to thermal runaway and loss of temperature control of the reactor. In addition to the safety implication of a thermal runaway there is the probability of catalyst damage/deactivation as a result of the high temperatures involved. One means of removing heat is described in the aforesaid EP-A-0685449, which is the provision within the fluid bed reactor of cooling tubes/coils which facilitate the transfer of heat from the reactor. However, using this method there is a physical limit to the amount of heat removable which is imposed by the number and size of the cooling tubes/coils that can be fitted in the reactor without affecting the fluidisation characteristics. The problem to be solved therefore is that of removing heat from the fluidised bed reactor without detrimentally affecting the operation of the fluidised bed process. We have found that the solution to the problem is to introduce a liquid into the fluidised bed reactor for the purpose of cooling the fluidised bed reactor by evaporation of the liquid, thereby utilising the latent heat of vaporisation of the liquid.

The removal of reaction heat by injection of liquid acetic acid into the fluidised bed reaction of acetylene and acetic acid in the presence of zinc acetate supported on activated carbon to produce vinyl acetate is known from Soviet Union Patent No. 384815. However, this process differs completely from the process forming the subject of the present invention principally in the respect that acetylene is used as a reactant rather than ethylene. Consequently the reaction exotherms differ considerably, the ethylene route to vinyl acetate has approximately double the heat of reaction of the acetylene route. Furthermore, since ethylene-based process catalysts differ substantially in nature from acetylene-based process catalysts their response to liquids in terms of wet quenching and defluidisation are unpredictable. It is not and never has been the practice in the fixed bed ethylene-based route to vinyl acetate to introduce the acetic acid reactant as a liquid to the catalyst bed, the belief being that such a measure would lead to catalyst deactivation.

Accordingly the present invention provides a process for the production of vinyl acetate by reacting at elevated temperature in a fluid bed reactor ethylene, acetic acid and an oxygen—containing gas in the presence of a fluid bed catalyst material characterised in that a liquid is introduced into the fluidised bed reactor for the purpose of removing heat therefrom by evaporation of the liquid.

The process of the present invention is advantageous in that it can reduce or eliminate altogether the number of cooling tubes/coils in the reactor, thereby facilitating the use of a smaller reactor, both of which have cost benefit implications. The process also allows the removal of a liquid vaporiser column and gas pre-heat exchangers, thereby improving the economics of the process.

It is essential that the liquid should vaporise within the fluidised bed reactor under the reaction conditions being employed for the production of vinyl acetate so that the desired cooling effect is obtained and to avoid substantial accumulation of liquid within the catalyst bed. Inevitably during start-up using catalysts having an adsorbent component, for example silica, when the catalyst is "dry" it will adsorb a certain amount of the liquid feed. However, under steady operating conditions substantially all of the liquid introduced into the fluidised catalyst bed evaporates therein such that any net accumulation of liquid within the fluidised catalyst bed is less than the wet quenching limit of the fluidised catalyst bed.

The liquid introduced into the fluidised bed reactor may suitably be a reactant, an inert liquid or a product of the reaction, or a mixture of any two or more thereof. Thus, at least a part of the acetic acid reactant may be fed to the fluidised bed reactor in liquid form. Alternatively, or in addition, at least some of the ethylene and/or oxygen may be introduced into the reactor in the form of a liquid, although in this case, to prevent damage to the catalyst, substantially all of the liquid ethylene and/or oxygen should evaporate (for example in a feed pipe or heat exchanger) before coming into contact with the fluid bed catalyst. Alternatively or in addition, an inert liquid, preferably one having a high latent heat of evaporation, may be employed. Suitable inert liquids include, for example, liquid hydrocarbons, such as pentane and hexane. Alternatively, or in addition, the liquid may be a product of the reaction. A suitable product is water, which is formed as a by-product of the reaction of ethylene, acetic acid and oxygen, because it has a relatively high latent heat of evaporation. Vinyl acetate product and/or acetaldehyde by-product may also be recycled and introduced in liquid form into the fluidised bed reactor.

The liquid may be introduced into the fluidised-bed reactor by suitably arranged injection means. A single injection means may be used or a plurality of injection means may be arranged within the fluidised bed reactor. For introducing liquid into the fluidised catalyst bed, the number of injection means used is that number which is required to provide sufficient penetration and dispersion of liquid at each injection means to achieve good dispersion of liquid across the fluidised catalyst bed. A preferred injection means is a nozzle or a plurality of nozzles which include gas-induced atomising nozzles in which a gas is used to assist in the injection of the liquid, or liquid-only spray-type nozzles. Alternatively, liquid may be introduced with the ethylene and/or oxygen-containing gas and/or recycle gas fed to the fluidised bed reactor suitably by bubbling the ethylene and/or oxygen-containing gas and/or recycle gas through the liquid prior to its introduction into the reactor. In a further alternative, liquid may be pumped into the area of the grid plate forming an essential component of a fluid bed reactor where contact with incoming ethylene and/or oxygen-containing gas and/or recycle gas would propel the liquid upwards into the fluidised catalyst bed. In yet a further alternative, liquid may be pumped into the reactor via a sparge bar or bars, optionally with one or more of the gaseous feeds.

In a preferred embodiment the present invention comprises a continuous process for the manufacture of vinyl acetate in a fluid bed reactor which comprises:

(i) feeding ethylene, acetic acid and an oxygen-containing gas into the fluid bed reactor, co-joining the ethylene, acetic acid and oxygen-containing gas at elevated temperature in the fluid bed reactor while in contact with a fluid bed catalyst material to enable the ethylene, acetic acid and oxygen-containing gas to react to produce vinyl acetate, normally liquid by-product comprising water and organic material and a gaseous by-product comprising carbon dioxide, (ii) removing from the reactor a gaseous effluent comprising unreacted ethylene, acetic acid and oxygen-containing gas, product vinyl acetate, normally liquid by-product and gaseous by-product, (iii) separating from the effluent removed from the reactor in (ii) a gaseous stream comprising ethylene, oxygen-containing gas and gaseous by-product from a stream comprising unreacted acetic acid, vinyl acetate product and normally liquid by-product and recycling the separated gaseous stream to the fluid bed reactor, (iv) separating in one or more operations the stream comprising unreacted acetic acid, vinyl acetate product and normally liquid by-product separated from the reactor effluent in (iii) into a fraction comprising vinyl acetate product and one or more fractions comprising unreacted acetic acid, vinyl acetate and normally liquid by-product, and (v) recovering vinyl acetate product and recycling a fraction comprising unreacted acetic acid and optionally vinyl acetate and/or normally liquid by-product to the fluid bed reactor, at least a part or all of one or more of (a) the acetic acid feed and (b) the recycled fraction comprising unreacted acetic acid and optionally vinyl acetate and/or normally liquid by-product being introduced as a liquid into the fluidised bed reactor.

In the continuous process described hereinabove reference is made to a normally liquid by-product, which is intended to define by-product which is a liquid under conditions of normal pressure and temperature, as opposed to a gas under such conditions. There is no intention to suggest that the by-product is removed from the reactor in the form of a liquid.

To maintain a controllable and constant reaction temperature it is necessary to balance heat removal with heat generated. This can be done by adding enough liquid to provide all the nett heat removal required (i.e. over and above that obtained by withdrawing product and introducing feeds and/or recycles from/to the reactor). However, in practice it is recognised that this will be difficult to control and could lead to excessive cooling of the liquids being fed to the reactor. This would lead to de-fluidisation and loss of reaction. This represents a safety hazard as ethylene and oxygen could then be mixed to form an explosive mixture. To overcome this potential problem it is desirable to use some cooling tubes/coils to provide "fine tuning" of the heat removal. Typically about 70% of the heat removal may be provided by liquid addition to the reactor. However, any appropriate percentage between 100 and greater than 0% of the heat removal may be by means of liquid additions to the reactor without exceeding the safety margins of the equipment operated.

It is recognised that vinyl acetate suppresses the reaction rate. Therefore, in the fixed bed production of vinyl acetate little or no vinyl acetate is returned to the reactor. However in fluid bed operation because the bed is thoroughly mixed, the impact of any vinyl acetate recycled to the reactor is less because vinyl acetate is present throughout the bed by virtue of the mixing. Therefore, the separation (iv) into a fraction comprising vinyl acetate product and one or more fractions comprising unreacted acetic acid and normally liquid by-product (which is recycled to the reactor) does not require to be so rigorous, thereby economising on separation plant costs.

Ethylene, acetic acid and an oxygen-containing gas are fed to the fluid bed reactor. Also fed to the reactor is a recycle gaseous stream comprising ethylene, oxygen-containing gas and gaseous by-product which has been separated from the effluent removed from the reactor and also a fraction comprising unreacted acetic acid and optionally vinyl acetate and/or normally liquid by-product separated in (iv). At least a part or all of one or more of (a) the acetic acid feed and (b) the recycled fraction comprising unreacted acetic acid and optionally vinyl acetate and/or normally liquid by-product, is introduced to the reactor in the form of a liquid. The feed and recycle components may be introduced to the reactor by a variety of different routes including the fluid bed reactor grid, sparge bars and liquid/gas feed nozzles. The components may be fed separately or in combination. Ethylene and acetic acid may be introduced to the reactor through one or more inlets and oxygen introduced through at least one further inlet. As mentioned hereinbefore liquid components may be introduced by gas-induced atomising nozzles in which a gas is used to assist in the injection of the liquid, or liquid-only spray type nozzles.

A suitable gas-induced atomising nozzle for use in the process according to the present invention comprises:

(a) at least one inlet for a pressurised liquid, (b) at least one inlet for an atomising gas, (c) a mixing chamber to mix said liquid and gas, and (d) at least one outlet through which said mixture is discharged.

The atomising gas may suitably be an inert gas, for example nitrogen or carbon dioxide. Preferably the atomising gas is either ethylene or oxygen feed or recycle gaseous stream or a mixture of two or more thereof. An advantage of using oxygen feed as the atomising gas is that the reactant that causes the "heat source" is delivered with the liquid which is used to "remove the heat", i.e. the liquid coolant is delivered to the point of maximum need. Another advantage of using oxygen as the atomising gas is that it eliminates the need for a separate sparge bar in the reactor bed to introduce oxygen, thereby simplifying plant design and improving fluidisation because there are fewer internals in the reactor. Alternatively, ethylene feed or a combination of ethylene feed and oxygen feed may be used as the atomising gas.

Each nozzle may be provided with a plurality of outlets of suitable configuration. The outlets may for example comprise circular holes, slots, ellipsoids or other suitable configurations. Each nozzle may comprise a plurality of outlets of varying configuration.

The size of the outlets is preferably such that there is little pressure drop therethrough.

The outlets are preferably symmetrically arranged around the circumference of each nozzle, but may also be arranged asymmetrically therein.

The atomising gas supply to each nozzle is maintained at a pressure sufficient to break the liquid into small droplets and to prevent particle ingress from the fluidised bed or particle blockage of the outlets of the nozzle.

The relative size of the mixing chamber is arranged to ensure optimum atomisation. The volume of the mixing (atomising) chamber relative to the volume of the liquid passing through the chamber expressed as:

Volume of mixing chamber (in cc)/Liquid flowrate (cc/sec) is suitably in the range from $5\times10^{-3}$ to $5\times10^{-1}$ seconds.

The velocity of the liquid is preferably maintained at a velocity sufficient to ensure that any particles, for example fines, do not separate out of the liquid stream.

The weight ratio of atomising gas:liquid supplied to each nozzle is typically in the range 1:99 to 25:75.

A gas-induced atomising nozzle suitable for use in the process of the present invention is described and illustrated in WO-A-94/28032.

A single nozzle or a plurality of nozzles may be employed. Preferably there is used a plurality of nozzles. The nozzle or nozzles may be located in the reactor grid or in the reactor walls above the grid.

A suitable liquid-only spray nozzle for use in the process according to the present invention comprises at least one inlet for pressurised liquid and at least one outlet for said pressurised liquid, sufficient liquid pressure being maintained within the nozzle to ensure that the liquid emerging from the outlet has the desired momentum to achieve adequate dispersion and penetration within the fluidised bed reactor.

The pressure drop in each nozzle can be regulated, if desired, by the use of restrictive devices such as valves.

The outlets may comprise similar configurations as defined above for the gas induced atomiser nozzles, a preferred configuration being circular holes. Further information pertaining to liquid-only spray nozzles may be found in the aforesaid WO-A-94/28032.

The introduction into the fluidised bed reactor of a liquid may be the sole means of removing heat from the reactor, or it may be supplemented by one or more other means of removing heat from the reactor. Suitable other means of removing heat from the reactor include the provision within the reactor of cooling tubes/coils and the passage of recycle gases and vapours from the reactor through external cooling tubes/coils or heat—exchanger prior to its reintroduction to the reactor.

Alternatively, or in addition, the liquid may be cooled (e.g. using refrigeration techniques) before being introduced into the reactor. This allows an even greater cooling effect in the reactor than is provided by the liquid evaporative effect alone. The further cooling of the liquid may be achieved by the use of suitable cooling means, for example a simple heat exchanger or refrigerator.

Commercial ethylene and acetic acid may be used in the process of the present invention with or without further purification. The oxygen—containing gas may be a gas richer or poorer in molecular oxygen than air, but is preferably substantially pure molecular oxygen. In operating the process regard must be had to minimising the explosion risk associated with the use of an oxygen-containing feed gas.

Any fluid bed catalyst material active for the conversion of ethylene, acetic acid and oxygen to vinyl acetate may be used in the process of the present invention. Suitable fluid bed catalyst materials and methods for their preparation are described, for example, in the aforesaid EP-A-Nos. 672453 and 685451. A suitable catalyst comprises palladium and one or more promoters selected from alkali metals, alkaline earth metals, transition metals and lanthanide metals supported on a suitable support, for example silica. Examples of promoter metals include potassium, sodium, barium, cadmium, antimony and lanthanum. The promoters are generally employed as solutions of suitable salts of the metals, for example carboxylate salts, typically acetates. For most promoters, for example potassium acetate, each should be maintained at a concentration of between 0.1 and 30 weight % on the catalyst.

In the fixed bed process for the production of vinyl acetate the acetic acid feed is vaporised with the gaseous feed. The catalyst bed loses promoter, e.g. potassium acetate, during the reaction. Accordingly, in the operation of a fixed bed process a small quantity of promoter solution is sprayed into the inlet gas stream to vaporise and replenish the promoter on the catalyst bed. This can be difficult and can lead to uneven promoter distribution which in turn can give rise to non-optimum catalyst performance. In the fluid bed process according to the present invention it is preferred to dissolve the promoter in the liquid feed to the bed. Because the bed is in motion, fluidised, the catalyst and promoter mix thereby reaching a uniform promoter concentration throughout the bed. This is clearly an improvement over fixed bed operation and should lead to improved productivity and selectivity because promoter levels can more easily be controlled. Catalyst samples can be removed from the reactor to monitor promoter levels and facilitate the adjustment of promoter feed levels in the liquid feed stream to maintain the appropriate level on the catalyst.

The ethylene, acetic acid and oxygen—containing gas are suitably reacted at elevated temperature, suitably within the range 100° to 250° C., preferably within the range from 135° to 195° C. The reaction is suitably accomplished at pressures, within the range from 0 to 300 psig, preferably within the range from 75 to 150 psig.

Gaseous feed concentrations of ethylene, acetic acid and oxygen may vary. Typically useful ranges in mole % are as follows:

| | |
|---|---|
| Ethylene | 30 to 70%, preferably 35 to 65%, most preferably 40 to 60%; |
| Acetic Acid | 10 to 25%, preferably 12 to 22%, most preferably 15 to 20%; and |
| Oxygen | 0 to 25% preferably 4 to 16% |

The balance of the feed (to make up to a total of 100 mol %) comprises gaseous inerts, e.g. carbon dioxide, ethane and argon, in the gaseous recycle stream and recycled normally liquid by-product.

The process of the present invention will now be illustrated by reference to the following examples.

EXAMPLE 1

By calculation it was found that if streams 1 and 2 from Table 1 were used in the fluid bed production of vinyl acetate by the catalysed reaction of ethylene, acetic acid and oxygen, and the streams were added to the fluid bed reactor in the vapour phase at 8 barg and 155° C., then for the stoichiometric reactions given in Table 2 reacting to the extents and conversions given in Table 3, about 8.7 MW of heat would be liberated. (The extent of reaction is defined as the number of moles generated for any component divided by the stoichiometric coefficient.)

If however stream 1 was added to the reactor at 155° C. and stream 2 was added such that 50% of the stream was in the liquid phase at 155° C., and the reactor was to be maintained at 155° C., the heat liberated would be reduced to about 3.7 MW.

These two calculations demonstrate that some of the heat liberated in the reaction is utilised to vaporise the liquid feed thereby reducing the overall heat removal requirements by other means, for example cooling tubes/coils.

TABLE 1

|  | Substream: Mixed Phase | |
| --- | --- | --- |
| Components Flows: Kg/Hr | Stream 1 | Stream 2 |
| Nitrogen ($N_2$) | 99 | 0 |
| Argon (Ar) | 69 | 0 |
| Oxygen ($O_2$) | 8567 | 0 |
| Methane ($CH_2$) | 11 | 0 |
| Ethylene ($C_2H_4$) | 39282 | 0 |
| Ethane ($C_2H_6$) | 25 | 0 |
| Carbon Dioxide ($CO_2$) | 20796 | 0 |
| Vinyl acetate | 0 | 4252 |
| Water ($H_2O$) | 0 | 10270 |
| Acetic acid | 0 | 29099 |
| Total Flow: (Kg/hr) | 68849 | 43621 |

TABLE 2

1. $C_2H_4 + C_2H_4O_2 + \frac{1}{2}O_2 \rightarrow C_4H_6O_2 + H_2O$
2. $C_2H_4 + 3O_2 \rightarrow 2CO_2 + 2H_2O$
3. $C_2H_4 + C_2H_4O_2 \rightarrow C_4H_8O_2$
4. $C_2H_4 + C_3H_6O_2 + \frac{1}{2}O_2 \rightarrow C_5H_8O_2 + H_2O$
5. $C_2H_4 + 2C_2H_4O_2 + \frac{1}{2}O_2 \rightarrow C_6H_{10}O_{4\ +\ H_2O}$

TABLE 3

| EXTENT REACTION 1 | 128.89 |
| --- | --- |
| EXTENT REACTION 2 | 8.03 |
| EXTENT REACTION 3 | 0.0593 |
| EXTENT REACTION 4 | 0.0146 |
| EXTENT REACTION 5 | 0.1204 |

Comparison Test

A fluid bed vinyl acetate reactor was operated at 8 barg and a bed temperature of 152° C. with a gas hourly space velocity of 116 $hr^{-1}$ (at process conditions). The catalyst had metal loadings of 0.44 Pd, 0.36 Au and 2.5K (weight %). The total feed composition was ethylene:acetic acid:oxygen:nitrogen, 52.9:9.9:7.6:29.6 as mole % respectively. The acetic acid was introduced to the reactor with the main gas inlet stream via a vaporiser at 150° C. through the bottom of the reactor. Bed temperatures are given in the accompanying Table 4.

An on-line oxygen analyser indicated that 45% of the oxygen had been converted to products.

This is not an example according to the present invention because none of the components was introduced to the reactor in the form of a liquid. It is included only for the purpose of comparison.

EXAMPLE 2

The Comparison Test was repeated except that the acetic acid was introduced to the reactor as a liquid at room temperature through a sparge pipe positioned towards the inlet of the reactor within the catalyst bed. Bed temperatures are given in the accompanying Table 4.

An on-line oxygen analyser indicated that 43% of the oxygen had been converted to products. This demonstrates that the Comparison Test and Example 2 produced almost identical heats of reaction.

Examination of Table 4 shows the effect of introducing a cold liquid direct to the catalyst bed on observed reaction exotherm. Reaction exotherm is taken as the temperature difference of the heater coils or oil between the system when operating with feed reagents without oxygen and the system when operating with oxygen feed. When the acetic acid feed is vaporised a reaction exotherm is observed throughout the bed. When the acetic acid is introduced as a liquid the reaction exotherm is substantially reduced in the bottom and middle sections of the bed. These results demonstrate that the direct addition of liquids to the reactor bed can remove some of the heat of reaction. The catalyst did not agglomerate and defluidise.

TABLE 4

| | Reactor Temperature (°C.) | | | | | |
|---|---|---|---|---|---|---|
| | Comparison Test | | | Example 2 | | |
| Position in reactor | Acetic acid vapour; no oxygen | Acetic acid vapour + 7.6 mole $O_2$ | Reaction exotherm | Acetic acid liquid; no oxygen | Acetic acid liquid + 7.6 mole $O_2$ | Reaction exotherm |
| Reactor bed top | | | | | | |
| Inside reactor | 152 | 152 | | 152 | 152 | |
| Inside reactor | 152 | 152 | | 152 | 152 | |
| Heater coil | 254 | 239 | 15 | 253 | 239 | 14 |
| Heater oil | 135 | 129 | 6 | 135 | 132 | 3 |
| Reactor bed middle | | | | | | |
| Inside reactor | 152 | 152 | | 152 | 151 | |
| Inside reactor | 152 | 152 | | 152 | 152 | |
| Heater coil | 228 | 222 | 6 | 231 | 228 | 3 |
| Heater oil | 140 | 136 | 4 | 139 | 138 | 1 |
| Reactor bed bottom | | | | | | |
| Inside reactor | 152 | 152 | | 151 | 150 | |
| Inside reactor | 152 | 152 | | 152 | 152 | |
| Heater coil | 249 | 240 | 9 | 251 | 251 | 0 |
| Heater oil | 141 | 134 | 7 | 141 | 140 | 1 |

We claim:

1. A process for the production of vinyl acetate by reacting at elevated temperature in a fluid bed reactor ethylene, acetic acid and an oxygen-containing gas in the presence of a fluid bed catalyst material characterised in that a liquid is introduce into the fluidised reactor for the purpose of removing heat therefrom by evaporation of the liquid.

2. By process as claimed in claim 1 wherein the liquid introduced into the reactor is a reactant, an inert liquid, a product of the reaction or a mixture thereof.

3. A process as claimed in claim 2 wherein the liquid is liquid ethylene, liquid oxygen, a liquid hydrocarbon, water, vinyl acetate or acetaldehyde.

4. A process as claimed in claim 1 wherein the liquid is introduced into the fluidised bed through injection means.

5. A process as claimed in claim 4 wherein the injection means is a gas-induced atomising nozzle.

6. A process as claimed in claim 4 wherein the injection means is a gas induced atomising nozzle and the atomising gas is selected from nitrogen, carbon dioxide, ethylene, oxygen feed, recycle gaseous stream or a mixture thereof.

7. A process as claimed in claim 1 wherein the catalyst comprises palladium and one or more promoters selected from alkali metals, alkaline earth metals, transition metals and lanthanide metals supported on a support.

8. A process as claimed in claim 7 wherein the promoter is selected from potassium, sodium, barium, cadmium, antimony and lanthanum.

9. A process as claimed in claim 7 wherein the promoter concentration is between 0.1 and 30 weight % on the catalyst.

10. A process as claimed in claim 7 wherein the promoter is dissolved in the liquid feed.

11. A process as claimed in claim 1 carried out at a temperature of from 100° to 250° C. and a pressure of 0 to 300 psig.

12. A process as claimed in claim 1 wherein the ethylene feed concentration is from 30 to 70 mole %, acetic acid feed concentration is 10 to 25 mole % and oxygen concentration is 0 to 25 mole %.

13. A process as claimed in claim 1 in which the process is continuous and comprises (i) feeding ethylene, acetic acid and an oxygen-containing gas into the fluid bed reactor, co-joining the ethylene, acetic acid and oxygen-containing gas at elevated temperature in the fluid bed reactor while in contact with a fluid bed catalyst material to enable the ethylene, acetic acid and oxygen-containing gas to react to produce vinyl acetate, normally liquid by-product comprising water and organic material and a gaseous by-product comprising carbon dioxide; (ii) removing from the reactor a gaseous effluent comprising unreacted ethylene, acetic acid and oxygen-containing gas, product vinyl acetate, normally liquid by-product and gaseous by-product; (iii) separating from the effluent removed from the reactor in (ii) a gaseous stream comprising ethylene, oxygen-containing gas and gaseous by-product from a stream comprising unreacted acetic acid, vinyl acetate product and normally liquid by-product and recycling the separated gaseous stream to the fluid bed reactor, (iv) separating in one or more operations the stream comprising unreacted acetic acid, vinyl acetate product and normally liquid by-product separated from the reactor effluent in (iii) into a fraction comprising vinyl acetate product and one or more fractions comprising unreacted acetic acid, vinyl acetate and normally liquid by-product, and (v) recovering vinyl acetate product and recycling a fraction comprising unreacted acetic acid and optionally vinyl acetate and/or normally liquid by-product to the fluid bed reactor; at least a part or all of (a) the acetic acid, and (b) the recycled fraction comprising unreacted acetic acid and optionally vinyl acetate and/or normally liquid by-product being introduced as a liquid into the fluidised bed reactor.

* * * * *

UNITED STATES PATENT AND TRADEMARK OFFICE
CERTIFICATE OF CORRECTION

PATENT NO. : 5,817,866
DATED : October 6, 1998
INVENTOR(S) : BRISTOW et al

It is certified that error appears in the above-identified patent and that said Letters Patent is hereby corrected as shown below:

Claim 3, line 2, insert --, liquid acetic acid,-- after "hydrocarbon"

Signed and Sealed this

Eighth Day of May, 2001

Attest:

NICHOLAS P. GODICI

Attesting Officer

Acting Director of the United States Patent and Trademark Office